(12) United States Patent
Chang et al.

(10) Patent No.: US 9,249,117 B2
(45) Date of Patent: Feb. 2, 2016

(54) **USE OF COMPOUNDS FROM *ANTRODIA CAMPHORATA* IN MANUFACTURING MEDICAMENTS FOR TREATING KIDNEY DISEASES**

(71) Applicant: Hui Ling Tseng, Taipei (TW)

(72) Inventors: Wen-Liang Chang, New Taipei (TW); Chen-Wen Yao, Taipei (TW); I-Chuan Yen, Taipei (TW); Hui Ling Tseng, Taipei (TW); Wan Ping Tseng, Taipei (TW); Tai Lin Tseng, Taipei (TW); Yin Yu Kuo, Taipei (TW)

(73) Assignee: Hui Ling Tseng, Taipei (TW)

( * ) Notice: Subject to any disclaimer, the term of this patent is extended or adjusted under 35 U.S.C. 154(b) by 0 days.

(21) Appl. No.: 14/624,015

(22) Filed: Feb. 17, 2015

(65) Prior Publication Data

US 2015/0336918 A1    Nov. 26, 2015

(30) Foreign Application Priority Data

May 20, 2014  (TW) ............... 103117608 A
May 20, 2014  (TW) ............... 103117609 A
May 20, 2014  (TW) ............... 103117610 A (51) Int. Cl.
*A61K 31/015*   (2006.01)
*C07D 307/20*   (2006.01)
*C07C 49/84*    (2006.01)

(52) U.S. Cl.
CPC ............. *C07D 307/20* (2013.01); *C07C 49/84* (2013.01)

(58) Field of Classification Search
CPC .... C07D 307/20; C07D 307/32; A61K 31/34; A61K 31/122; A61K 31/015; C07C 49/84
USPC .......................................... 549/475; 514/764
See application file for complete search history.

(56) References Cited

FOREIGN PATENT DOCUMENTS

WO    WO2012/100228    *   7/2012   ........... A61K 31/122

OTHER PUBLICATIONS

Lee, Tzong-Huei at al., "A new cytotoxic agent from solid-state fermented mycelium of Antrodia camphorata" from Planta letter 2007; 73: 1412-1415.
Yang, Sien-Sing et al. "New constituents with iNOS inhibitory activity from mycelium of Antrodia camphorata" from Planta Med. Apr. 2009; 75(5):512-6.

* cited by examiner

*Primary Examiner* — T. Victor Oh
(74) *Attorney, Agent, or Firm* — WPAT, P.C.; Anthony King (57) ABSTRACT

The present invention provides a use of compounds from *Antrodia camphorata* in manufacturing medicaments for treating kidney diseases, wherein the compounds is represented by formula (I):

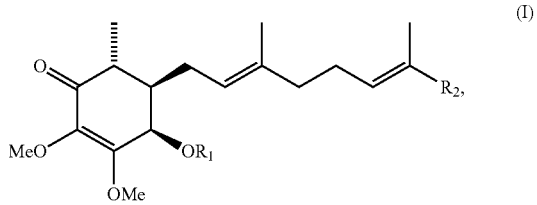

wherein $R_1$ is a hydrogen atom or acetyl group, $R_2$ is

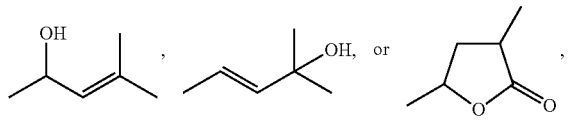

wherein the kidney disease is glomerulosclerosis or glomerulonephritis.

3 Claims, 6 Drawing Sheets

USE OF COMPOUNDS FROM *ANTRODIA CAMPHORATA* IN MANUFACTURING MEDICAMENTS FOR TREATING KIDNEY DISEASES

BACKGROUND OF THE INVENTION

1. Field of the Invention

The present invention relates to a medical use of compounds isolated from *Antrodia camphorata*, in particular to a use of manufacturing medicaments for treating kidney diseases.

2. The Prior Arts

*Antrodia camphorata* is also called Chang-Zhi, Niu Chang-Gu, red camphor mushroom and the like, which is a perennial mushroom belonging to the order Aphyllophorales, the family Polyporaceae. The *Antrodia camphorata* is a unique Formosan fungal growing on the inner wall of the rotten cavity *Cinnamomum kanehirai* Hay. *Cinnamoum kanehirai* Hay is rarely distributed and overcut unlawfully, which makes *Antrodia camphorata* parasitizing inside the tree in the wild become even rare. The price of *Antrodia camphorata* is very expensive due to the extremely slow growth rate of the fruiting body that only grows between June to October. In traditional Taiwanese medicine, *Antrodia camphorata* has effects on antidote, antidiarrhea, anti-inflammation, liver diseases treatment, anti-cancer and the like. *Antrodia camphorata* like general edible-medicinal mushrooms is rich in numerous complicated components, in which the well-known bioactive components are included triterpenoids, polysaccharides (such as β-D-glucan), vitamins (such as vitamin B, nicotinic acid), protein (immunoglobulin), superoxide dismutase (SOD), trace element (such as calcium, phosphorous, germanium), nucleic acid, sterols and stabilizers for blood pressure (such as antodia acid) and the like. These bioactive components are believed to exhibit effects such as: anti-tumor activities, increasing immuno-modulating activities, anti-allergy, anti-bacteria, anti-high blood pressure, decreasing blood sugar, decreasing cholesterol and the like. Wherein particular components which have been discovered in the recent years may have effects on anti-inflammation, especially treating kidney diseases.

General speaking, the common kidney diseases mean the functions of kidney are influenced by attacking the glomerulus. The glomerulus diseases which include numerous symptoms due to various genes and environment conditions, mainly classify into glomerulosclerosis and glomerulonephritis. Glomerulosclerosis is a sclerosis of glomerulus in kidney. Generally, it is an injury of blood capillary, glomerulus in kidney, and kidney functional unit which is used to filter urine from blood. Proteinuria (most amount of protein in urine) is one of the signs of glomerulosclerosis. The kidney injuries can influence the filtering function of kidney and cause proteins to leak from blood into urine. However, glomerulosclerosis is merely one of numerous factors to lead proteinuria. In addition, kidney biopsy may be a necessary indication for determining whether a patient suffers from glomerulosclerosis or another kidney disease. Glomerulosclerosis, especially means focal segmental glomerulosclerosis (FSGS) and nodular glomerulosclerosis.

Focal segmental glomerulosclerosis (FSGS) is determined by the injured characteristics of focal segmental sclerosis and foot process effacemen. The research in the past twenty years shows that the incidence of an end-stage kidney disease suffered by the patients with FSGS is about 13 to 78 percent. Although the causes and sources of FSGS are not clearly, but mainly due to visceral epithelial cell injuries, which lead to complicated reaction in glomerulus, and then cause glomerulosclerosis.

Nephropatia diabeica or intercapillary glomerulonephritis also called as diabetic nephropathy or Kimmelstiel-Wilson syndrome, is a progressive kidney disease which is caused by angiopathy of capillaries in kidney glomerulus. This disease is characterized by nephrotic syndrome and diffuse glomerulosclerosis or suffering from diabetes mellitus for long time. In addition, a primary treatment in many countries is dialysis.

Up to now, steroids and immunosuppressive medicaments are mainly used to treat primary FSGS, but these developing therapies are still limited for treating the kidney injuries because of various side effects. As a result, the therapies are just based on experience rules rather than pathologic evidences.

Glomerulonephritis is an inflammation in the kidney membranes which have functions for filtrating wastes and unwanted fluids from blood.

The most common glomerulonephritis is IgA nephropathy (IgAN). The cause leading to accelerate the development of glomerulonephritis is not able to predict, prevent and treat clinically. Therefore, it is considered the main factor which could develop chronic kidney failure of kidney diseases. As a result, even the other immune, clinical, pathological factors can cause kidney failure in the patient's kidneys who suffer from IgAN, but abnormal increases of systemic T cell activation, lumphocyte/macrophage/neutrophil are also considered one of main process which cause IgAN to transfer to the chronic kidney failure. Moreover, oxidative stress is also considered a main process which causes IgAN to increase and develop in the patients and the animal model. There has been reported that reactive oxygen species (ROS) can directly lead to disease in most human and experimental kidney diseases.

Although glucocorticoid is widely used to treat the patients suffering from IgAN. However, the effects of glucocorticoid in maintaining the kidney function of IgAN and in lowering the urinary protein are not clear. The side effects of leading to potential uncontrollable inhibited immune response due to use glucocorticoid steroid for long periods of time also make medical problems.

It has been known that extractions from *Antrodia camphorata* contain various medical effects from recent numerous experiments, wherein the compositions of extractions from the *Antrodia camphorata* have also been analyzed. However, it is an issue to be solved that whether the extractions from *Antrodia camphorata* contain any other compounds for efficiently treating kidney diseases.

SUMMARY OF THE INVENTION

Accordingly, the present invention is mainly for six compounds extracted from *Antrodia camphorata*, and to determine whether said compounds have effects for treating diseases and anti-inflammation of kidney.

An objective of the present invention is to provide a medical use of compounds from *Antrodia camphorata* to manufacture medicaments for treating kidney diseases, wherein the compound is represented by formula (I):

wherein $R_1$ is a hydrogen atom or acetyl group, $R_2$ is wherein the kidney disease is glomerulosclerosis or glomerulonephritis.

Preferably, wherein the compound is represented by formula (II):

(II)

Preferably, wherein the compound is represented by formula (III):

(III)

Preferably, wherein the compound is represented by formula (IV):

(IV)

Preferably, wherein the compound is represented by formula (V):

(V)

Preferably, wherein the glomerulosclerosis is focal segmental glomerulosclerosis (FSGS) or nodular nephrosclerosis.

Preferably, wherein the glomerulonephritis is IgA nephropathy (IgAN).

In the aforementioned compounds, Antrocamol LT1, Antroquinonol B and 4-acetyl-antroquinonol B all exhibit anti-oxidative effects to the nephritis cells. In addition, Antrocamol LT3 exhibits excellent effect for inhibiting the MCP-1 level. Therefore, the above compounds of *Antrodia camphorata* can be used to produce medicaments in the future, and are desired to exhibit anti-inflammatory effects for treating the kidney diseases including glomerulosclerosis and glomerulonephritis, especially for focal segmental glomerulosclerosis (FSGS), nodular nephrosclerosis, and IgA nephropathy (IgAN).

DETAILED DESCRIPTION OF THE PREFERRED EMBODIMENT

The present invention was mainly about the six kinds of compounds extracted from *Antrodia camphorata*, and to determine whether said compounds had the effects for treating diseases and anti-inflammation of kidney, wherein Antrocamol LT1, Antrocamol LT2, and Antrocamol LT3 were new compounds discovered by the inventor, and their extraction and structural identification were presented below. Although Antroquinonol, Antroquinonol B, 4-acetyl Antroquinonol B, and Antrocamol LT3 had been discovered, their effects for treating diseases and anti-inflammation in kidney had not been taught before. Accordingly, the relevant experiments of those compounds are also performed in the present invention.

The extraction and structural identification of the three compounds: Antroquinonol, Antroquinonol B, and 4-acetyl Antroquinonol B could refer to the following references: Lee et al., "A new cytotoxic agent from solid-state fermented mycelium of *Antrodia camphorata*". Planta letter 2007; 73: 1412-1415; and Yang et al., "New constituents with iNOS inhibitory activity from mycelium of *Antrodia camphorata*". Planta Med. 2009 April; 75(5):512-6. Therefore, the details about those compounds will not be discussed here again.

Extraction of *Antrodia camphorata*

The mycelium or fruiting body or mixture of both taken from *Antrodia camphorata* (1.0 kg) were double extracted by 10 times alcohol and then concentrated to obtain about 230 g crude product (LT-E). The crude product was operated 3 times by partition extraction with dichloromethane/water to form a dichloromethane layer about 102.6 g (LT-E-D) and a water layer about 127.4 g (LT-E-W). Then, 6.0 g of the dichloromethane layer was separated to four layers with ANCA-E-D-1, ANCA-E-D-2, ANCA-E-D-3, and ANCA-E-D-4 by silica column chromatography with solvents which were n-hexane/dichloromethane (1:4), dichloromethane, and methanol/dichloromethane (5:95).

According to the aforementioned results, ANCA-E-D-2 and ANCA-E-D-3 were further purified. ANCA-E-D-3 was flushed by preparative reverse-phase chromatography (C-18 reverse-phase column) using 80% MeOH/H₂O, and then about 150 mg of new compound, Antrocamol LT1, was obtained at about 18.75 minutes. ANCA-E-D-2 was flushed by preparative reverse-phase chromatography (C-18 reverse-phase column) using 80% MeOH/H₂O, and then about 170 mg of a new compound, Antrocamol LT2, was obtained at about 25.10 minutes. ANCA-E-D-3 was flushed by reverse-phase chromatography (C-18 preparative column) using 80% MeOH/H₂O as a elution, and then about 180 mg of Antrocamol LT3 was obtained at about 14.5 minutes.

Antrocamol LT1 was a colorless liquid product, and it was analyzed and found that its molecular formula was $C_{24}H_{38}O_5$ with a molecular weight of 406. The complete name of this compound was called 4-hydroxy-5-[9-hydroxy-3,7,11-trimethyldodeca-2,6,10-trienyl]-2,3-dimethoxy-6-met hyl-cyclohex-2-enone.

Antrocamol LT1 structural identification spectra were presented below: $^1$H-NMR (400 MHz, CDCl₃): 1.12 (3H, d, J=7.2 Hz,), 1.61 (3H, s), 1.64 (3H, s), 1.66 (3H, s), 1.68 (3H, s), 1.72 (1H, m), 1.98-2.30 (8H), 2.51 (1H, dq, J=11.6, 7.2 Hz), 3.62 (3H, s), 4.02 (3H, s), 4.33 (1H, d, J=2.8 Hz), 4.35 (1H, dt, J=9.2, 4.0 Hz), 5.09 (1H, d, J=8.4 Hz), 5.14 (1H, t, J=7.2 Hz), 5.15 (1H, t, J=7.2 Hz); $^{13}$C-NMR (100 MHz, CDCl₃): 12.17 (q), 15.95 (q), 16.19 (q), 18.13 (q), 25.72 (q), 25.93 (t), 26.78 (t), 39.41 (t), 39.98 (d), 43.29 (d), 47.94 (t), 58.81 (q), 60.48 (q), 65.35 (d), 67.24 (d), 121.64 (d), 127.64 (d), 128.42 (d), 132.03 (s), 134.99 (s), 135.97 (s), 137.42 (s), 160.82 (s), 197.15 (s).

Antrocamol LT2 was a colorless liquid product, and it was analyzed and found that its molecular formula was $C_{26}H_{40}O_6$ with a molecular weight of 448. The complete name for this compound was called 4-acetoxy-5-[9-hydroxy-3,7,11-trimethyldodeca-2,6,10-trienyl]-2,3-dimethoxy-6-met hyl-cyclohex-2-enone.

Antrocamol LT2 structural identification spectra were presented below: $^1$H-NMR (400 MHz, CDCl₃): ☐1.18 (3H, d, J=7.2 Hz,), 1.54 (3H, s), 1.64 (3H, s), 1.67 (3H, s), 1.69 (3H, s), 1.72 (1H, m), 1.80-2.40 (8H), 2.50 (1H, dq, J=11.6, 7.2 Hz), 3.65 (3H, s), 3.98 (3H, s), 4.36 (1H, m), 5.10 (1H, t, J=6.8 Hz), 5.12 (1H, d, J=8.0 Hz), 5.20 (1H, t, J=6.4 Hz), 5.72 (1H, t, J=3.2 Hz); $^{13}$C-NMR (100 MHz, CDCl₃): 12.80 (q), 15.96 (q), 16.09 (q), 18.14 (q), 20.93 (q), 25.72 (q), 26.19 (t), 26.76 (t), 39.47 (t), 41.25 (d), 42.98 (d), 48.12 (t), 59.65 (q), 60.67 (q), 65.53 (d), 68.98 (d), 120.74 (d), 127.42 (d), 128.25 (d), 131.74 (s), 134.70 (s), 137.31 (s), 137.56 (s), 158.21 (s), 169.73 (s), 196.84 (s).

Antrocamol LT3 was a colorless liquid product, and it was analyzed and found that its molecular formula was $C_{24}H_{38}O_5$ with a molecular weight of 448. The complete name for this compound was called(4R,5R,6R)-4-hydroxy-5-[(2E,6E,9E)-11-hydroxy-3,7,11-trimethyldodeca-2,6,9-trienyl]-2,3-dimethoxy-6-methylcyclohex-2-enone.

Antrocamol LT3 structural identification spectra were presented below: $^1$H-NMR (400 MHz, CDCl₃): 1.14 (3H, d, J=7.2 Hz,), 1.29 (6H, s), 1.56 (3H, s), 1.63 (3H, s), 1.70 (1H, m), 2.02 (2H), m), 2.08 (2H, t, J=6.4 Hz), 2.21 (2H, t, J=7.6 Hz), 2.51 (1H, dq, J=11.2, 7.2 Hz), 2.64 (1H, d, J=5.2 Hz), 3.64 (3H, s), 4.05 (3H, s), 4.32 (1H, d, J=3.2 Hz), 5.08 (1H, t, J=6.8 Hz), 5.14 (1H, t, J=6.4 Hz), 5.57 (2H, m); $^{13}$C-NMR (100 MHz, CDCl₃): 12.32 (q), 16.14 (q), 16.14 (q), 26.35 (t), 26.95 (t), 29.85 (q), 39.63 (t), 40.24 (d), 42.20 (t), 43.40 (d), 59.29 (q), 60.59 (q), 67.88 (d), 70.76 (d), 121.14 (d), 124.78 (d), 125.22 (d), 134.04 (s), 135.84 (s), 137.77 (s), 139.17 (d), 160.59 (s), 197.21 (s).

Cell Culture Method

Here, Mouse MC line CRL-1927 was used in order to proceed the subsequent experiments. The cell line was derived from American Type Culture Collection (Rockville, Md., USA), and then was operated regular culture with a culture medium consisted of Dulbecco's modified Eagle's medium and Ham's F-12 medium with 3:1 ratio, and adding 5% fetal bovine serum and 14 mM HEPES.

Cell Survival Determination

The aforementioned cell line was cultured in the culture medium for 24 hours. The cells after hyperplasia were washed once with PBS, and treated with 1 time trypsin-EDTA, and followed by centrifuging at 1,200 rpm for 5 minutes, and the cells sedimented to form the cell pellet and the supernatant was removed. Then, 10 ml fresh medium was added, and the cells were re-suspended by shaking slightly. The cells were placed in 96-well microplate. When they were tested, 0.01~200 µg/ml compounds from *Antrodia camphorata* were added into each of the well. The cells were incubated at 37° C. with 5% $CO_2$ for 48 hours. Subsequently, 5 mg/ml 3-(4,5-dimethylthiazol-2-yl)-2,5-diphenyltetrazolium bromide (MTT) were added into the each well to react in the dark environment for 2 hours. Furthermore, in order to calculate the survival rate of the cells, the absorbance at wavelength of 570 nm was determined by enzyme-linked immunosorbent assay, and then the needed concentration for the half growth inhibition ratio (IC50) was calculated. All the experimental data were presented as the standard value with plus/minus the standard deviation. The experimental data was performed by statistical analysis with paired-t test. When the p value is smaller than 0.05, it was considered as differences in statistics.

By using mesangial cells in the six compounds from *Antrodia camphorata* for MTT cell viability assay, the results were presented in FIGS. 1A-1F. The results indicated that recent all the chosen concentrations of Antroquinonol, Antrocamol, Antrocamol LT1, Antrocamol LT2, Antrocamol LT3, Antroquinonol B, and 4-acetyl-Antroquinonol B did not affect mesangial cells to grow.

Anti-Oxidation/Anti-Inflammation of Compounds Form *Antrodia camphorata*

It is known that glomerulosclerosis and glomerulonephritis are caused by serious inflammation. The leucocytus aggregating by immune response will release amount of ROS to produce oxidative stress in the kidney cells, and then injure kidney. Therefore, the decrease or the elimination of oxidative stress in the kidney cells is one of the methods for treating kidney diseases. To decrease ROS in cells is also an important index for treating the aforementioned kidney diseases.

Determination of Reactive Oxygen Species (ROS)

Determination of ROS was by detecting the intensity of fluorescence from an oxide of 2',7'-dichlorofluorescein diacetate (2',7'-dichlorofluorescein diacetate). The mesangial cells was treated as compounds which are to be measured, and 2',7'-dichlorofluorescein diacetate (2 µM) was added to react for 30 minutes. After reaction for 30 minutes, LPS was added at specific time. Then, the signals were determined by absorption spectrometer (Bio-Rad Laboratories, Inc) with exciting wavelength of 485 nm and emitting wavelength of 530 nm. It indicated that the higher ROS content as the more intensive fluorescence.

Because ROS was inseparably related to kidney diseases, the results for determination of ROS in the aforementioned cells were shown in FIG. 2A-2F.

Figure 1A:
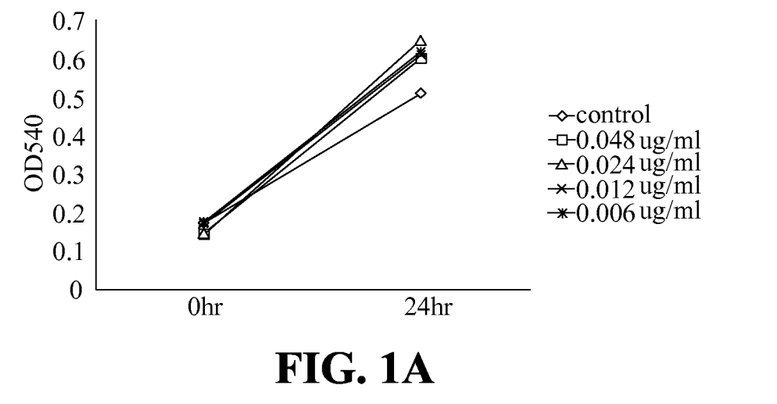
FIGS. 1A-1F represented the results of MTT cell viability assay by using mesangial cell on the six kinds of compounds from *Antrodia camphorata*.
Figure 1B:
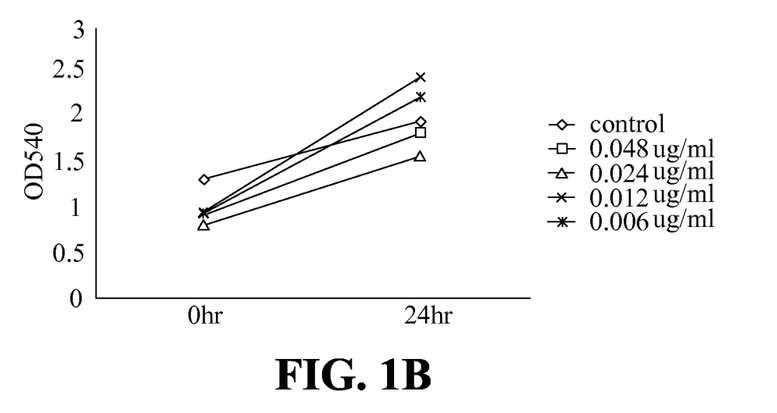
Figure 1C:
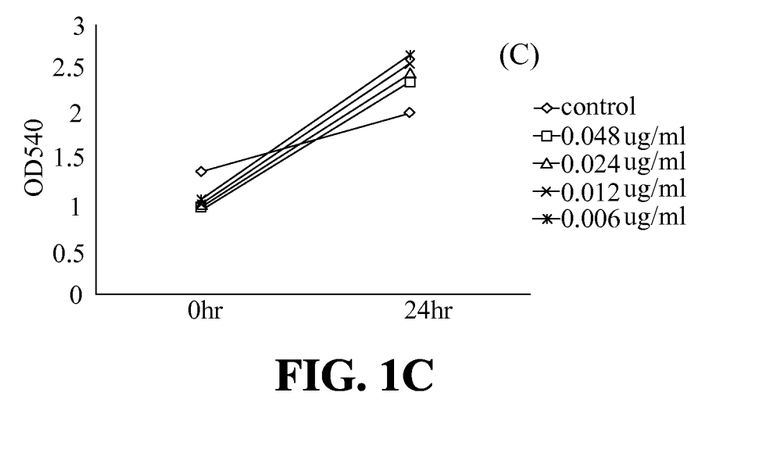
Figure 1D:
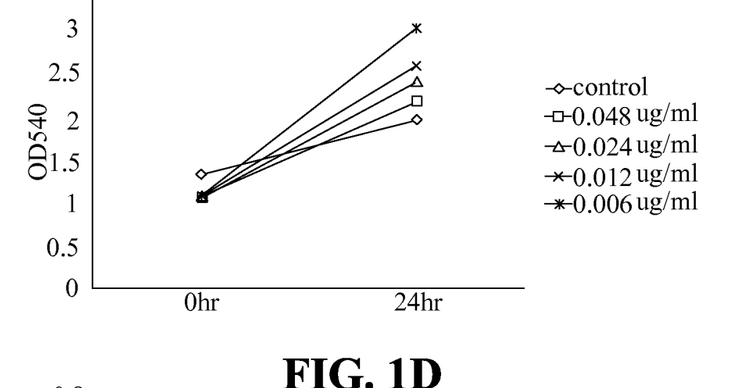
Figure 1E:
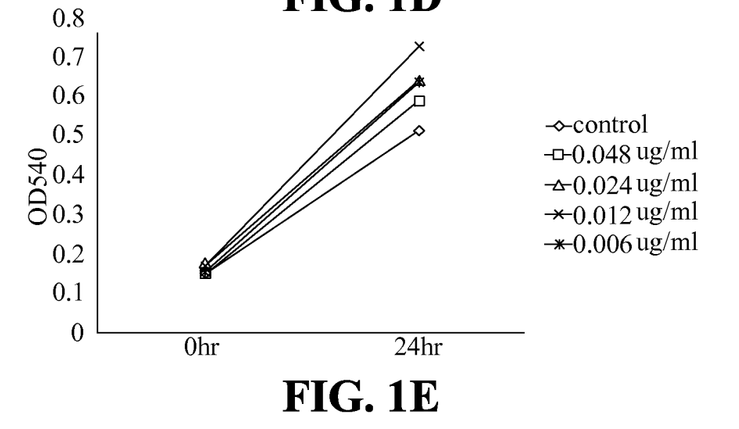
Figure 1F:
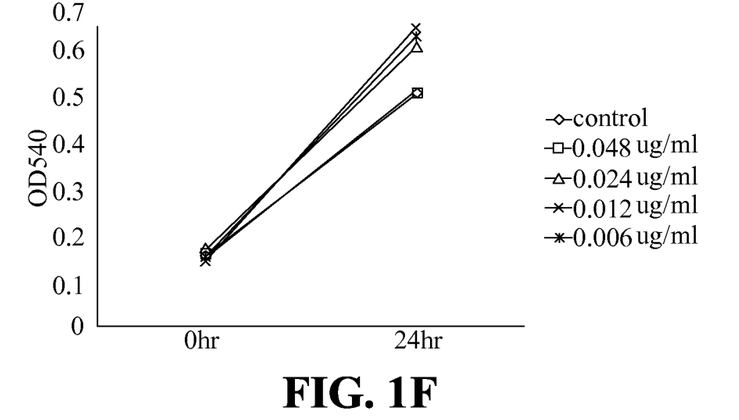
Figure 2A:
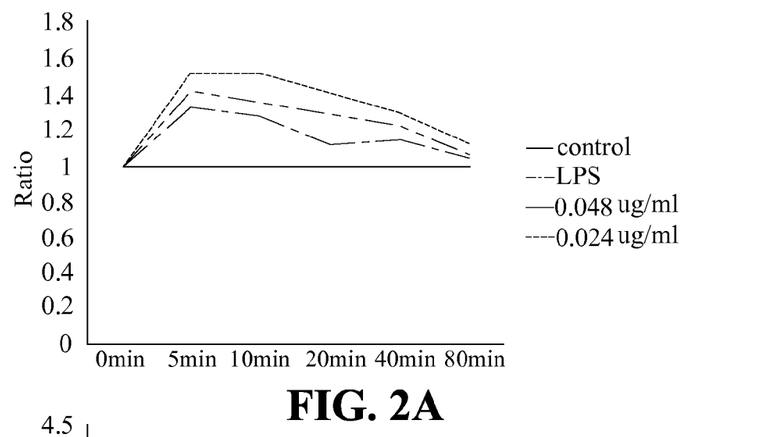
FIGS. 2A-2F represented the the results of anti-oxidative determination for the six kinds compounds from *Antrodia camphorata*.

Referring to FIG. 2A, 0.012 µg/ml and 0.048 µg/ml of Antroquinonol were used respectively to analyze the effect for inhibiting ROS. The results indicated that current concentrations did not have the inhibiting effect in 5 minutes.

Figure 2B:
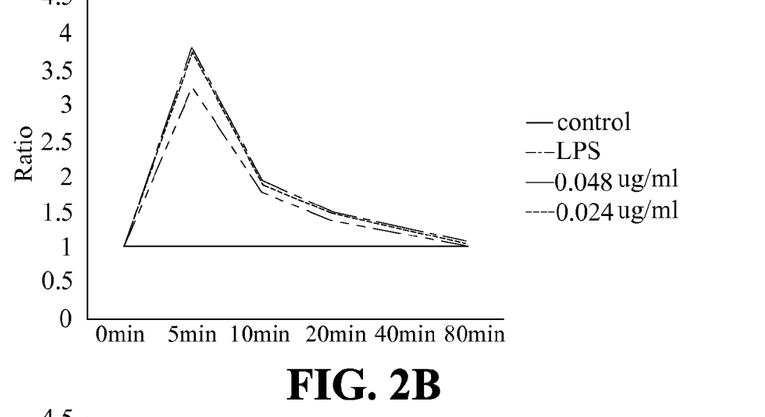

Referring to FIG. 2B, 0.012 μg/ml and 0.048 μg/ml of Antrocamol LT1 were used respectively to analyze the effect for inhibiting ROS. The results indicated that 0.012 μg/ml of Antrocamol LT1 could inhibit 3% ROS, and 0.048 μg/ml of Antrocamol LT1 could inhibit 14% ROS in 5 minutes.

Figure 2C:
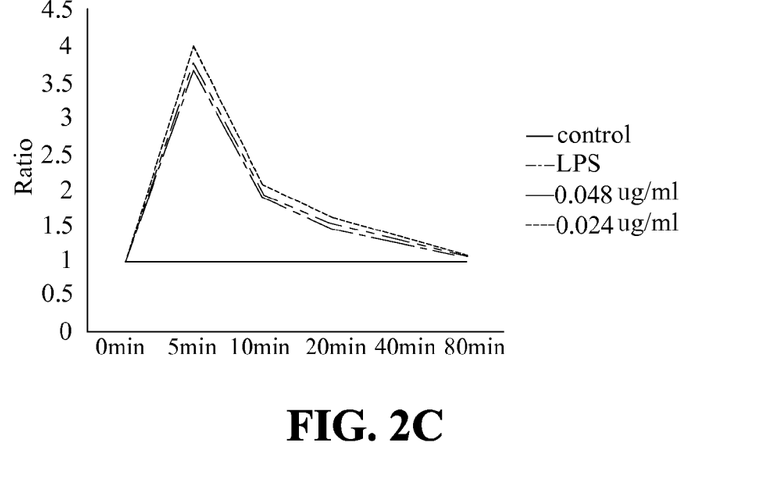

Referring to FIG. 2C, 0.012 μg/ml and 0.048 μg/ml of Antrocamol LT1 were used respectively to analyze the effect for inhibiting ROS. The results indicated that the current concentrations did not have the inhibiting effect in 5 minutes.

Figure 2D:
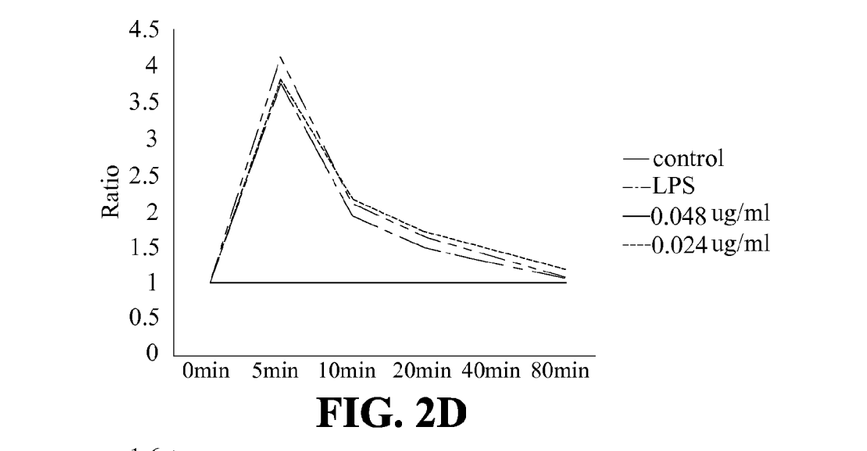

Referring to FIG. 2D, 0.012 μg/ml and 0.048 μg/ml of Antrocamol LT3 were used respectively to analyze the effects for inhibiting ROS. The results indicated that current concentrations did not have the inhibiting effect in 5 minutes.

Figure 2E:
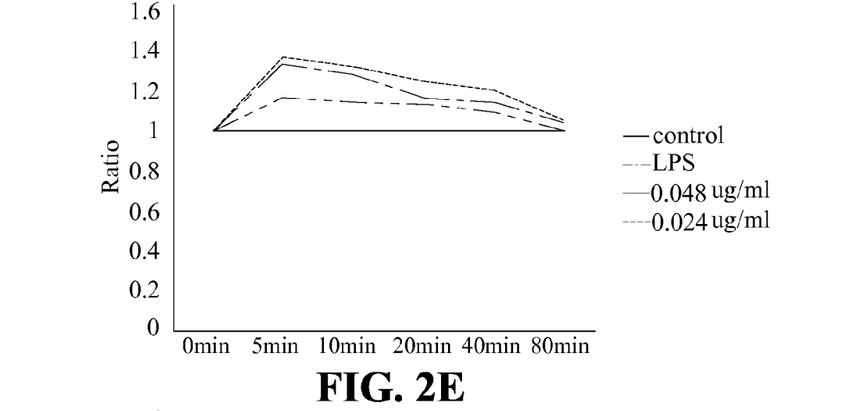

Referring to FIG. 2E, 0.012 μg/ml and 0.048 μg/ml of Antroquinonol B were used respectively to analyze the effects for inhibiting ROS. The results indicated that 0.048 μg/ml of Antroquinonol B could inhibit 12.5% ROS in 5 minutes.

Figure 2F:
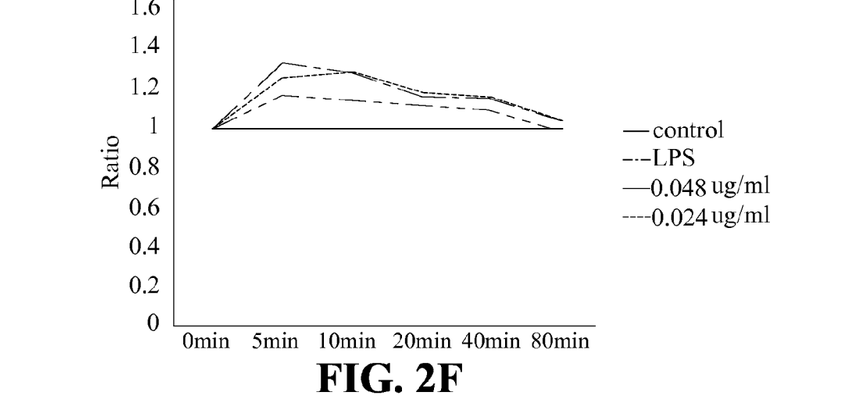

Referring to FIG. 2(F), 0.012 μg/ml and 0.048 μg/ml of 4-acetyl-Antroquinonol B were used respectively to analyze the effects for inhibiting ROS. The results indicated that 0.012 μg/ml of Antrocamol LT1 could inhibit 3% ROS in 5 minutes, and 0.048 μg/ml of Antrocamol LT1 could inhibit 14% ROS in 5 minutes.

The results were presented in Table 1.

TABLE 1

| Sample Index | Concentration for Testing | Inhibiting ROS % |
| --- | --- | --- |
| Antroquinonol | 0.048 μg/ml | 0% |
|  | 0.012 μg/ml | 0% |
| LT1 | 0.048 μg/ml | 14% |
|  | 0.012 μg/ml | 3% |
| LT2 | 0.048 μg/ml | 0% |
|  | 0.012 μg/ml | 0% |
| LT3 | 0.048 μg/ml | 0% |
|  | 0.012 μg/ml | 0% |
| Antroquinonol B | 0.048 μg/ml | 12.5% |
|  | 0.012 μg/ml | 0% |
| 4-acetyl-Antroquinonol B | 0.048 μg/ml | 12% |
|  | 0.012 μg/ml | 5% |

Anti-Inflammation of Compounds from *Antrodia camphorata*

It is known that MCP1 plays an important role in interstitial inflammation, tubular atrophy, and kidney fibrosis. Therefore, by performing the protein test, the effects of *Antrodia camphorata* about anti-inflammation for the cells in kidney can be determined.

According to the manual, MCP-1 in the supernatant was detected by ELISA kits (Biosciences, Los Angeles, Calif., USA) and was determined by ELISA reader (Bio-Tek) (for wavelength absorbance of 450 nm). * * * indicated as $p<0.005$, NS indicated.

Figure 3A:
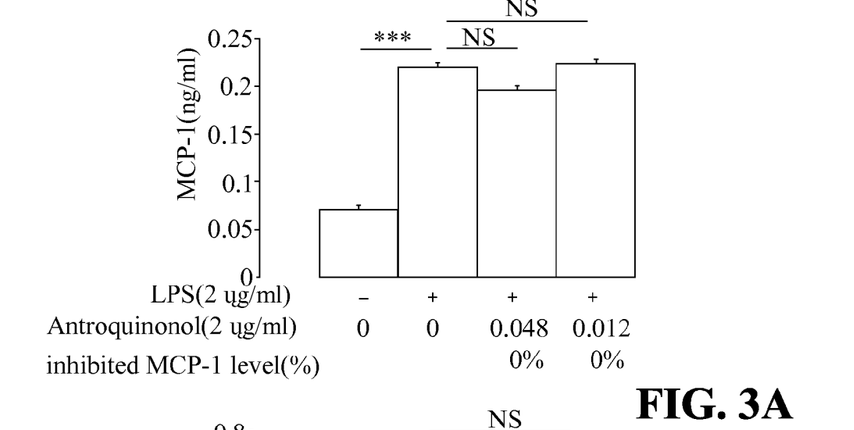
FIGS. 3A-3F represented the the results of anti-inflammatory response (MCP-1) for the six kinds of compounds from *Antrodia camphorata*.

Referring to FIG. 3A, 0.012 μg/ml and 0.048 μg/ml of Antroquinonol were used respectively to analyze the reaction about anti-inflammation (MCP-1). The results indicated that the current concentrations did not have the effects of inhibition.

Figure 3B:
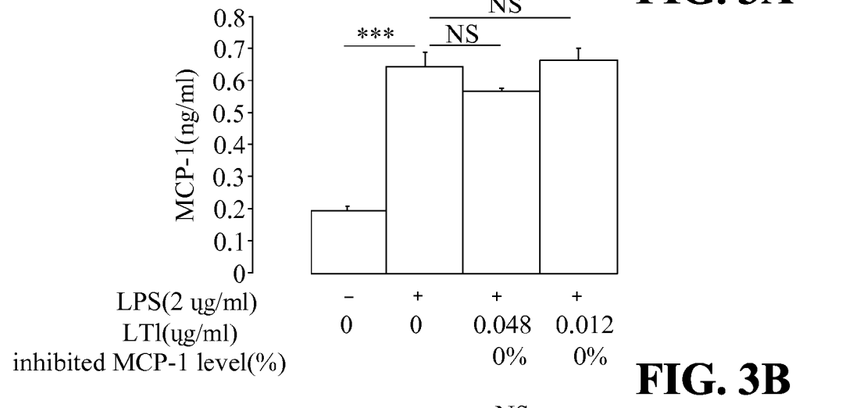

Referring to FIG. 3B, 0.012 μg/ml and 0.048 μg/ml of Antrocamol LT1 were respectively used to analyze the reaction about anti-inflammation (MCP-1). The results indicated that the current concentrations did not have the effects of inhibition.

Figure 3C:
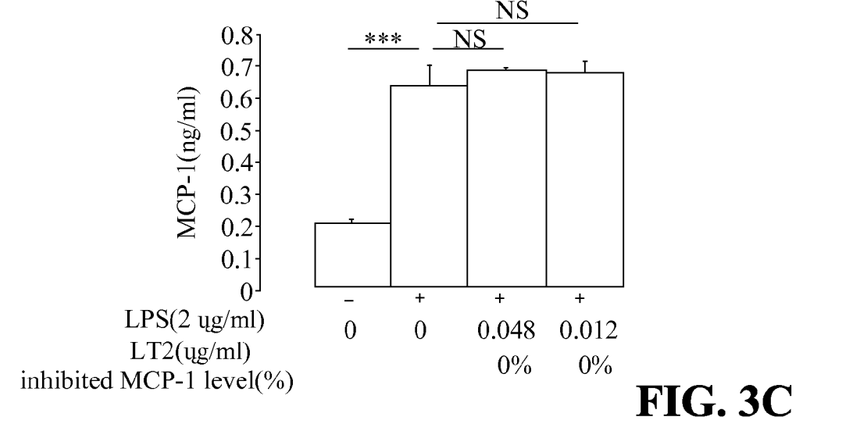

Referring to FIG. 3C, 0.012 μg/ml and 0.048 μg/ml of Antrocamol LT2 were used respectively to analyze the reaction about anti-inflammation (MCP-1). The results indicated that the current concentrations did not have the effects of inhibition.

Figure 3D:
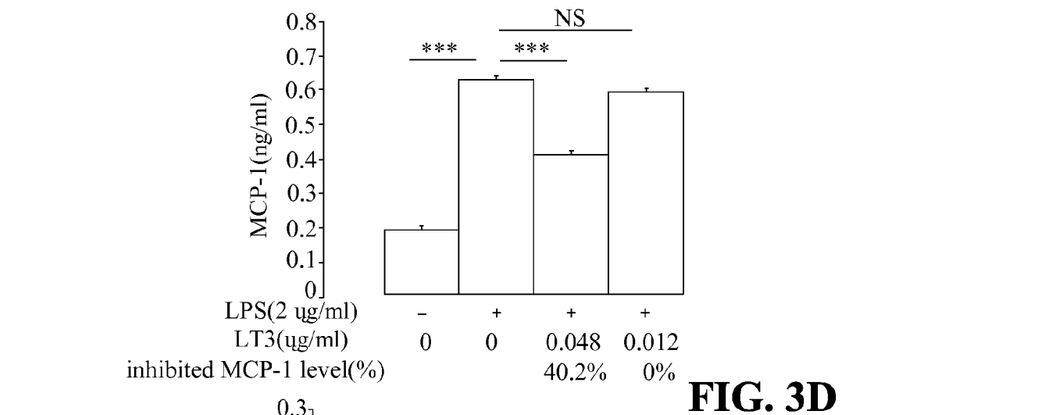

Referring to FIG. 3D, 0.012 μg/ml and 0.048 μg/ml of Antrocamol LT3 were used respectively to analyze the reaction about anti-inflammation (MCP-1). The results indicated that 0.048 μm/ml concentration could inhibit inflammation for 40.2%.

Figure 3E:
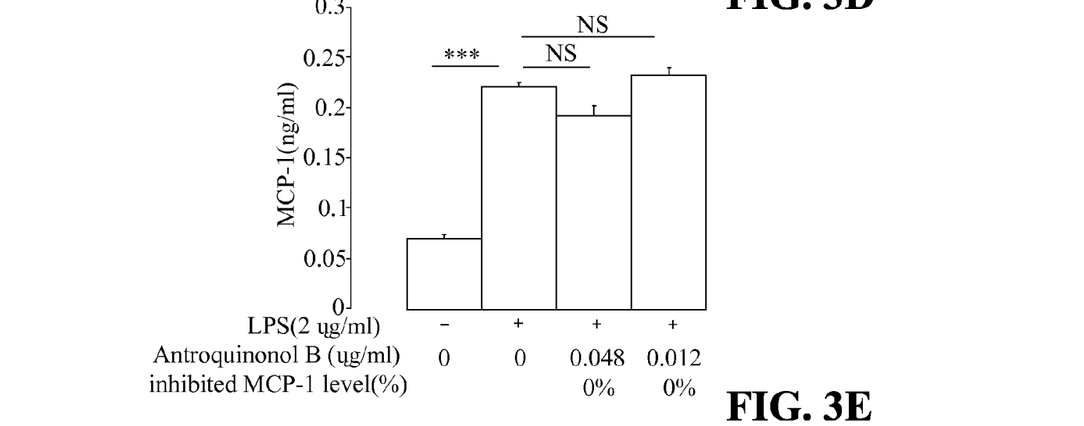

Referring to FIG. 3E, 0.012 μg/ml and 0.048 μg/ml of Antroquinonol B were used respectively to analyze the reaction about anti-inflammation (MCP-1). The results indicated that the current concentrations did not have the effects of inhibition.

Figure 3F:
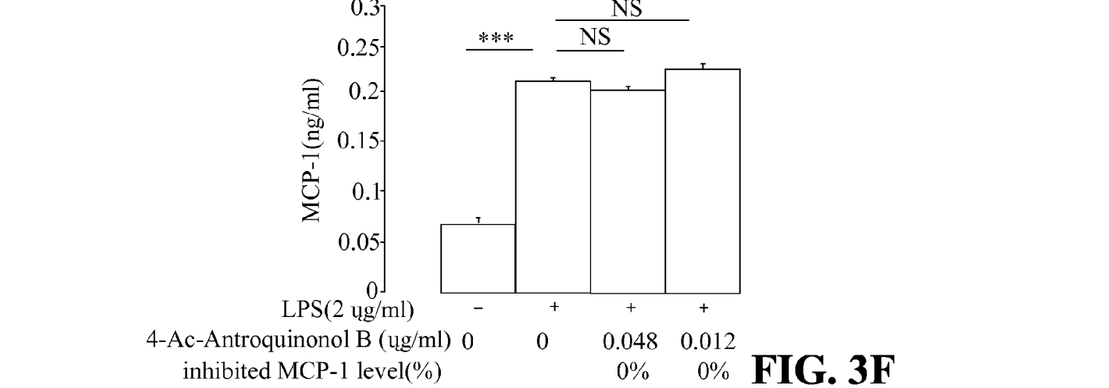

Referring to FIG. 3F, 0.012 μg/ml and 0.048 μg/ml of Antroquinonol B were used respectively to analyze the reaction about anti-inflammation (MCP-1). The results indicated that the current concentrations did not have the effects of inhibition.

The results were shown in Table 2.

TABLE 2

| Sample Index | Concentration for Testing | Inhibited MCP-1 level |
| --- | --- | --- |
| Antroquinonol | 0.048 μg/ml | 0% |
|  | 0.012 μg/ml | 0% |
| LT1 | 0.048 μg/ml | 0% |
|  | 0.012 μg/ml | 0% |
| LT2 | 0.048 μg/ml | 0% |
|  | 0.012 μg/ml | 0% |
| LT3 | 0.048 μg/ml | 40.2% |
|  | 0.012 μg/ml | 0% |
| Antroquinonol B | 0.048 μg/ml | 0% |
|  | 0.012 μg/ml | 0% |
| 4-acetyl-Antroquinonol B | 0.048 μg/ml | 0% |
|  | 0.012 μg/ml | 0% |

According to the aforementioned experimental results, wherein Antrocamol LT1, Antroquinonol B and 4-acetyl-Antroquinonol B exhibited anti-oxidation for nephritis cells by ROS test in the cells or inhibiting MCP-level. Antrocamol LT3 had better effect for inhibiting MCP-1 level. Therefore, the aforementioned compounds from *Antrodia camphorata* would be used to manufacture medicaments for treating kidney diseases in the future and expectedly had effect of anti-inflammation for currently well-known kidney diseases including glomerulosclerosis and glomerulonephritis, especially focal segmental glomerulosclerosis (FSGS), nodular glomerulosclerosis, and IgA nephropathy (IgAN).

Although Antroquinonol and Antrocamol LT2 in the six compounds were not discovered any anti-oxidative or anti-inflammatory effects, and should not be included in the scope of the present invention. However, by comparison, it further proved that the other four compounds extracted from *Antrodia camphorata* were precious because of their effects for the anti-inflammation.

The use of compounds from *Antrodia camphorata* in manufacturing medicaments for treating kidney diseases provided by the invention actually contains useful value on industry. It is not to be limited in scope by the specific embodiments described herein. Indeed, various modifications of the invention in addition to those described herein will be apparent to those skilled in the art from the foregoing description. Such modifications are intended to fall within the scope of the appended claims.

What is claimed is:

1. A method for treating a kidney disease in a subject in need thereof, comprising administering to the subject an effective amount of a compound from *Antrodia camphorata*, wherein the compound is represented by formula II:

2. The method of claim 1, wherein the glomerulosclerosis is focal segmental glomerulosclerosis (FSGS) or nodular nephrosclerosis.

3. The method of claim 1, wherein the glomerulonephritis is IgA nephropathy (IgAN).

* * * * *